(12) United States Patent
Kmiec, Jr.

(10) Patent No.: US 11,446,073 B2
(45) Date of Patent: Sep. 20, 2022

(54) FLEXIBLE SHAFT SUPPORT ROD

(71) Applicant: DEPUY SYNTHES PRODUCTS, INC., Raynham, MA (US)

(72) Inventor: Stanley J. Kmiec, Jr., West Chester, PA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 449 days.

(21) Appl. No.: 16/551,154

(22) Filed: Aug. 26, 2019

(65) Prior Publication Data

US 2021/0059736 A1    Mar. 4, 2021

(51) Int. Cl.
*A61B 17/88* (2006.01)
*A61B 17/72* (2006.01)
*A61B 17/00* (2006.01)

(52) U.S. Cl.
CPC ...... *A61B 17/8875* (2013.01); *A61B 17/7233* (2013.01); *A61B 2017/00867* (2013.01); *A61B 2017/00946* (2013.01)

(58) Field of Classification Search
CPC ...... A61B 17/1631; A61B 2017/00867; A61B 2017/0034; A61B 17/3417; A61B 17/3496; A61B 17/3472; A61B 2017/00309; A61B 17/7208; A61B 17/8875; A61B 17/1633; A61M 2025/006; B25B 23/0028; B08B 9/045
See application file for complete search history.

(56) References Cited

U.S. PATENT DOCUMENTS

| | | | | |
|---|---|---|---|---|
| 1,315,806 A | * | 9/1919 | Wilson | F16D 3/20 464/153 |
| 3,203,285 A | * | 8/1965 | Schmidt | B25G 1/025 81/177.6 |
| 3,585,885 A | * | 6/1971 | Carr | B25G 1/02 81/57 |
| 3,789,841 A | * | 2/1974 | Antoshkiw | A61M 25/09033 600/585 |
| 4,003,369 A | * | 1/1977 | Heilman | A61M 25/09 600/585 |
| 4,245,645 A | * | 1/1981 | Arseneault | A61B 5/283 600/378 |
| 4,676,249 A | * | 6/1987 | Arenas | A61M 25/09025 600/434 |

(Continued)

*Primary Examiner* — David W Bates
(74) *Attorney, Agent, or Firm* — Fay Kaplun & Marcin, LLP (57) ABSTRACT

A support rod for a hollow, flexible torque transmitting shaft for treating a bone includes support and flex portions. When the rod is received at a desired position within the shaft, the support portion extends through a first non-bendable portion of the shaft. An outer diameter of the support portion substantially corresponds to an inner diameter of the shaft to support the first portion. When the support rod is received at the desired position, the flex portion extends through a second bendable portion of the shaft. The flex portion includes a holding portion having an outer diameter substantially corresponding to an inner diameter of the second portion and a gap portion having an outer diameter reduced relative to the outer diameter of the holding portion to form an annular gap between the gap portion and an inner surface of the holding portion.

18 Claims, 5 Drawing Sheets

(56) References Cited

U.S. PATENT DOCUMENTS

| | | | | |
|---|---|---|---|---|
| 4,934,380 A * | 6/1990 | de Toledo | A61M 25/09 | 600/434 |
| 5,406,960 A * | 4/1995 | Corso, Jr. | A61M 25/09 | 600/434 |
| 5,455,997 A * | 10/1995 | Nasiell | B25B 13/481 | 29/456 |
| 5,488,761 A * | 2/1996 | Leone | B21K 1/12 | 29/2.25 |
| 5,497,785 A * | 3/1996 | Viera | A61M 25/09 | 600/434 |
| 5,788,653 A * | 8/1998 | Lorenzo | A61M 25/0905 | 600/585 |
| 5,788,654 A * | 8/1998 | Schwager | A61M 25/09 | 600/585 |
| 5,908,423 A * | 6/1999 | Kashuba | A61B 17/164 | 606/80 |
| 5,911,715 A * | 6/1999 | Berg | A61M 25/0043 | 604/525 |
| 6,048,339 A * | 4/2000 | Zirps | A61M 1/84 | 604/525 |
| 6,656,195 B2 * | 12/2003 | Peters | A61B 17/32002 | 606/159 |
| 6,862,958 B2 * | 3/2005 | Schade | B25B 23/0021 | 403/223 |
| 7,850,623 B2 * | 12/2010 | Griffin | A61M 25/0051 | 600/585 |
| 8,425,537 B2 * | 4/2013 | Mitelberg | A61B 17/12022 | 606/139 |
| 8,449,526 B2 * | 5/2013 | Snyder | A61M 25/0054 | 604/525 |
| 8,784,336 B2 * | 7/2014 | Bown | A61M 25/0127 | 600/585 |
| 9,545,252 B2 * | 1/2017 | Howard | A61B 17/1684 | |
| 10,022,131 B1 * | 7/2018 | Burley | A61B 17/1633 | |
| 10,933,221 B2 * | 3/2021 | Lepak | A61M 25/0138 | |
| 11,052,226 B2 * | 7/2021 | Salahieh | A61M 25/0136 | |
| 2005/0090849 A1 * | 4/2005 | Adams | A61B 17/320016 | 606/180 |
| 2008/0188854 A1 * | 8/2008 | Moser | A61B 17/0401 | 606/80 |
| 2010/0239380 A1 * | 9/2010 | Amirov | A61B 17/164 | 407/119 |
| 2011/0022069 A1 * | 1/2011 | Mitusina | A61B 17/32002 | 606/180 |
| 2011/0054487 A1 * | 3/2011 | Farnan | A61B 17/3478 | 606/108 |
| 2013/0231654 A1 * | 9/2013 | Germain | A61B 17/3472 | 606/33 |
| 2015/0174368 A1 * | 6/2015 | Garrison | A61M 29/00 | 604/525 |
| 2015/0374418 A1 * | 12/2015 | Martin | A61B 17/1615 | 606/291 |
| 2016/0051306 A1 * | 2/2016 | Sasaki | A61B 17/1659 | 606/93 |
| 2016/0228131 A1 * | 8/2016 | Brockman | A61B 17/1617 | |
| 2017/0056979 A1 * | 3/2017 | Krause | B25B 23/0021 | |
| 2017/0071631 A1 * | 3/2017 | Phillips | A61B 17/1633 | |
| 2017/0112552 A1 * | 4/2017 | Sinnott | A61B 17/1655 | |
| 2017/0113024 A1 * | 4/2017 | Hess | A61B 17/8897 | |
| 2017/0202563 A1 * | 7/2017 | Leroy | A61B 17/1642 | |
| 2018/0065235 A1 * | 3/2018 | Krause | A61B 17/8875 | |
| 2018/0311709 A1 * | 11/2018 | Rowe | A61B 90/70 | |
| 2019/0069908 A1 * | 3/2019 | Zilberman | A61B 17/1631 | |
| 2020/0030001 A1 * | 1/2020 | Shang | A61B 17/3439 | |
| 2020/0030624 A1 * | 1/2020 | Shang | A61N 5/0601 | |
| 2021/0113239 A1 * | 4/2021 | Donovan | A61B 18/1206 | |
| 2021/0153913 A1 * | 5/2021 | Walsh | A61F 2/447 | |

* cited by examiner

FLEXIBLE SHAFT SUPPORT ROD

FIELD OF THE INVENTION

The present disclosure relates generally to devices facilitating the treatment bones and, in particular, to allow the delivery of torque along a flexible shaft.

BACKGROUND

Procedures for the treating bones often require the application of torque to sites which are difficult to reach along a straight path. As one example, a trochanteric implant may be locked into an intramedullary nail by a set screw that needs to be rotated into position to lock the implant in a desired position relative to the nail. These set screws are often accessed via a lumen in the nail that, depending on the approach via which the nail was inserted into the body, may be reached only along a curved path. Flexible shafts employed for these purposes are often stiffened by inserting a rod through a guide wire lumen of the shaft as without such a stiffening rod pig tailing and torque loss have been observed with thinner shafts inserted along curved paths.

SUMMARY OF THE INVENTION

The present disclosure relates to a support rod for a hollow, flexible torque transmitting shaft for treating a bone comprising a support portion configured so that, when the support rod is received at a desired position within the hollow shaft, extends through a first portion of a length of the hollow shaft that is not configured to bend in use, an outer diameter of the support portion substantially corresponding to an inner diameter of the flexible shaft to support the first portion of the shaft and flex portion configured so that, when the support rod is received at the desired position within the hollow shaft, extends through a second portion of a length of the hollow shaft that is configured to bend in use, the flex portion including a holding portion having an outer diameter substantially corresponding to an inner diameter of the second portion of the hollow shaft and a gap portion having an outer diameter reduced relative to the outer diameter of the holding portion to form an annular gap between the gap portion and an inner surface of the holding portion.

The present disclosure also relates to a system for treating a bonea hollow, flexible torque transmitting shaft and a support rod. The support rod is sized and shaped to be received within the shaft, the rod including a support portion configured so that, when the rod is received at a desired position within the shaft, extends through a first portion of a length of the shaft that is not configured to bend in use, an outer diameter of the support portion substantially corresponding to an inner diameter of the shaft to support the first portion and a flex portion configured so that, when the rod is received at the desired position within the shaft, extends through a second portion of a length of the shaft that is configured to bend in use, the flex portion including a holding portion having an outer diameter substantially corresponding to an inner diameter of the second portion and a gap portion having an outer diameter reduced relative to the outer diameter of the holding portion to form an annular gap between the gap portion and an inner surface of the holding portion.

DETAILED DESCRIPTION

The present invention may be further understood with reference to the following description and the appended drawings, wherein like elements are referred to with the same reference numerals. Exemplary embodiments describe devices and procedures for applying torque along curved paths. As used herein, the terms distal and proximal refer to a direction away from a user of the device (distal) and toward a user of the device (proximal). The embodiments herein are described in relation to the use of a flexible shaft to apply torque to a set screw locking a trochanteric implant into an intramedullary nail. However, as would be understood by those skilled in the art, the embodiments described herein may be applied to any situation in which torque must be applied via a shaft that extends along a curved path while delivering the torque.

Figure 1:
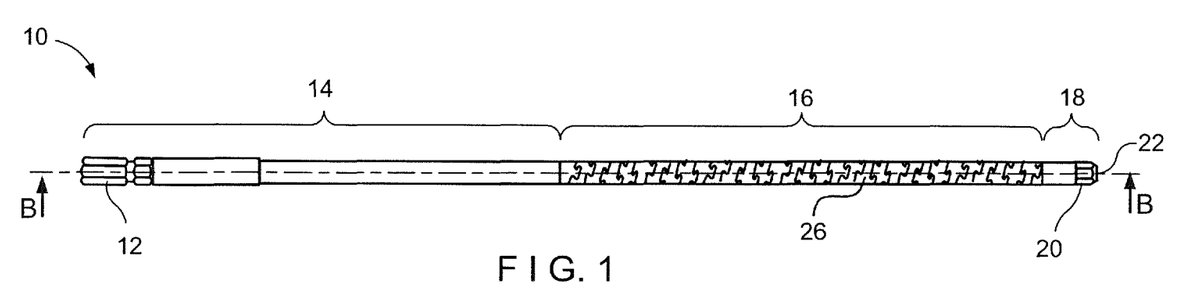
FIG. 1 shows a perspective view of an exemplary flexible shaft.
Figure 2:
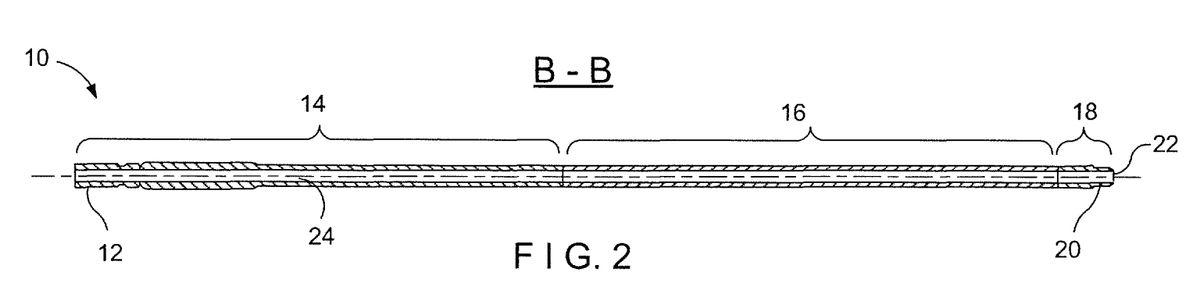
FIG. 2 shows a cross-sectional view of the shaft of FIG. 1 along line B-B.

As shown in FIGS. 1 and 2 a flexible shaft 10 for the delivery of torque extends from a proximal end 12 configured for attachment to a source of torque. In this embodiment, the proximal end 12 is configured as a hex coupling. The shaft 10 includes a relatively rigid proximal portion 14 extending from the proximal end 12 to a proximal end of a flexible portion 16 of the shaft 10. A distal portion 18 of the shaft 10 extends distally from the flexible portion 16 and includes a short relatively rigid section and a distal coupling 20 at a distal end 22 configured to engage an element to which the torque is to be delivered. In this embodiment, the distal coupling 20 is configured as a hex coupling to engage a set screw. However, those skilled in the art will understand that any suitable couplings may be employed for the proximal end 12 and the distal coupling 20. As seen in FIG. 2. A lumen 24 extends through the shaft 10 substantially along a axis illustrated by the line in FIG. 1. The lumen 24 in the shaft 10 is sized to receive a guide wire therein but may be sized at any diameter required for a particular procedure. In this embodiment an inner diameter of the lumen 24 is approximately 1 mm although other sizes may be contemplated without departing from the scope of this embodiment. The outer diameter of the shaft 10 of this embodiment is approximately Ø6.1 mm resulting in a wall thickness of approximately 1.4 mm.

The flexible portion flexible portion 16 has been treated to enhance the flexibility of this portion of the length of the shaft 10. For example, in this embodiment the flexible portion 16 has been laser etched along a substantially helical path 26 with interlocking notch and groove portions 28. As would be understood by those skilled in the art, other treatments or constructions of the shaft 10 may be employed to achieve the desired flexibility. At times, when a guide wire has been inserted into the shaft 10 several problems may arise. First, inserting the guide wire into the shaft 10 may increase the rigidity of the resulting combination that might increase the minimum bending radius of the shaft 10 rendering it unsuitable for certain applications. Alternatively, the guide wire itself may be plastically deformed if the shaft 10 is bent around too tight a radius. As mentioned above, if the shaft 10 is inserted with the lumen 24 empty, the shaft 10, when inserted along a curved path to a location at which torque must be applied may coil or pig tail or a substantial amount of the torque applied to the proximal end 12 may be lost over the length of the shaft 10 before reaching the distal coupling 20. In use, a bending angle of approximately 40 degrees is the most that would occur.

Figure 3:
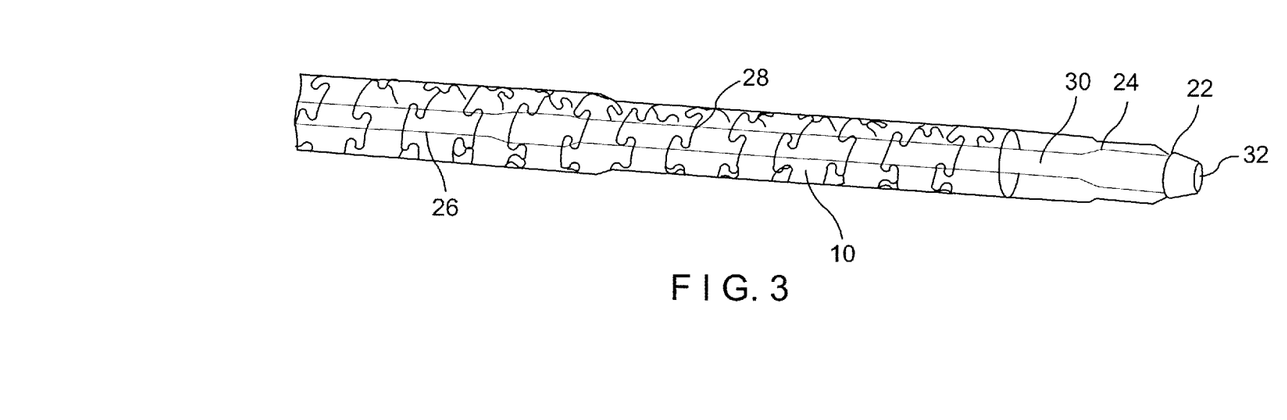
FIG. 3 shows a perspective view of a support rod inserted in the flexible shaft of FIG. 1.
Figure 4:
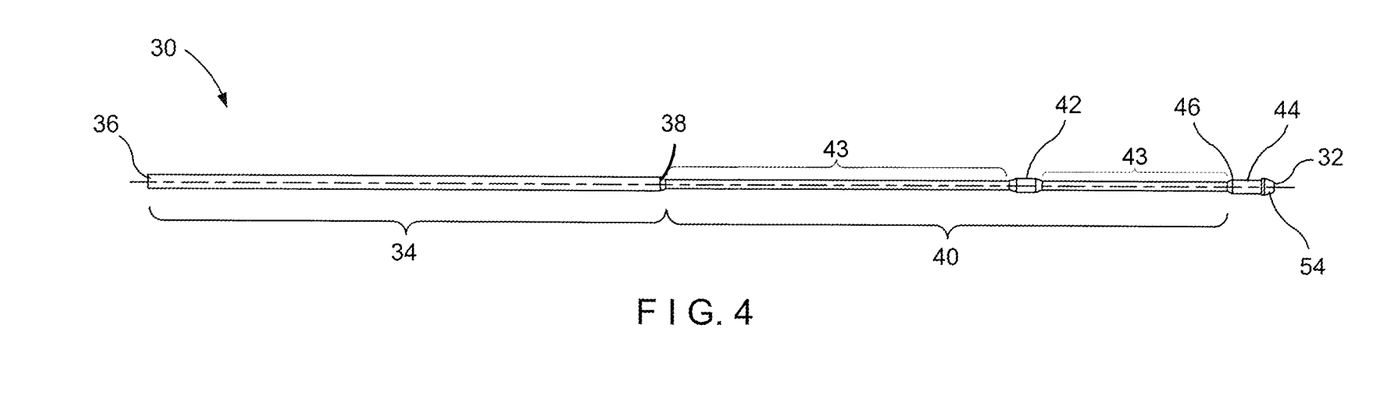
FIG. 4 shows a side view of a flexible rod according to a first embodiment.

As shown in FIGS. 3-6, a support rod 30 according to a first embodiment is inserted into a shaft 10 as described above. The support rod 30 extends within the lumen 24 so that a distal tip 32 of the rod 30 is seated at a distal end of the lumen 24 and projects slightly from the distal end 22 of the shaft 10. As shown in FIG. 4, the rod 30 includes a large diameter portion 34 (e.g., a proximal portion) that extends from a proximal end 36 to a shoulder 38 that necks the outer diameter of the rod 30 down from the increased diameter of the large diameter portion 34 to a reduced diameter that extends throughout a distal portion 40 relieved only by a first support portion 42 (e.g., a holding portion) having a diameter substantially equal to that of the large diameter portion 34. For the present embodiment, the rod 30 is 285 mm in length with the large diameter portion 34 being 135 mm in length and the distal portion 40 being approximately 142 mm in length.

Figure 5:
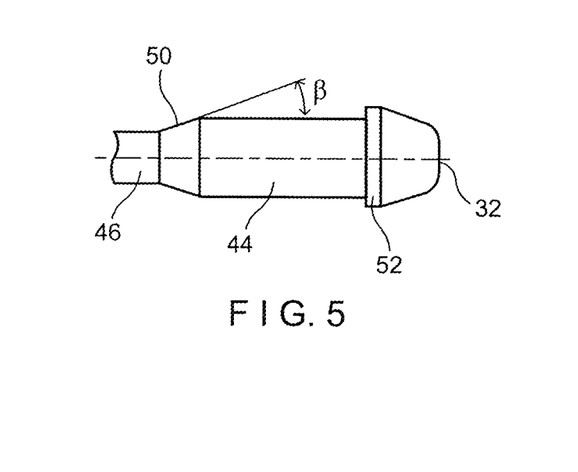
FIG. 5 shows a close up of a distal end of the rod of FIG. 4.
Figure 6:
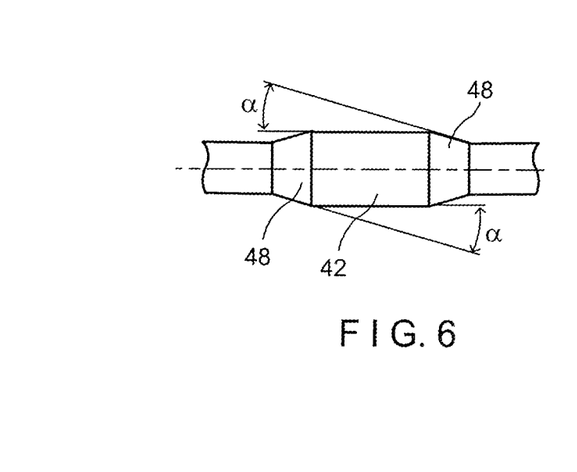
FIG. 6 shows a close up of an increased diameter section of the rod of FIG. 4.

Although in this embodiment the first support portion 42 is substantially centered within the distal portion 40 those skilled in the art will understand that it may be positioned in any location desired to obtain the required support while permitting the shaft 10 to bend as required for a particular procedure. For example, the first support portion 42 may be formed along the rod 30 at a position which, when the rod 30 is received within the shaft 10 with the distal tip 32 seated at the distal end of the lumen 24, is located away from a location on the rod corresponding to a particularly tight bending radius. A second support portion 44 extends distally from a distal end 46 of the distal portion 40 to the distal tip 32. The second support portion 44 of this embodiment also has an outer diameter substantially equal to that of the large diameter portion 34 and the first support portion 42. Thus, when the rod 30 is seated in the shaft 10 as desired, the large diameter portion 34 fits snugly within the lumen 24 while a gap portion 43 is formed between an outer surface of the distal portion 40 except at the first support portion 42 and the second support portion 44.

The first and second support portions 42 and 44, respectively, also fit snugly within the lumen 24. In addition, the distal portion 40 is positioned along the rod 30 so that, when the rod 30 is positioned within the shaft 10 with the distal tip 32 seated at the distal end of the lumen 24, the distal portion 40 extends within the flexible portion 16 of the shaft 10. The reduced diameter of the distal portion 40 forms an annular gap between the inner surface of the shaft 10 and the outer surface of the rod 30. This gap permits the flexible shaft 10 to bend around tight bending radii while the snug fit of the first and second support portions 42, 44, respectively, support the shaft 10 preventing the shaft 10 from pig-tailing and facilitating the transfer of torque along the shaft 10. The rod 30 is preferably malleable (elastically deformable) or of low flex strength and formed of, for example, nitinol or 304 annealed stainless steel although those skilled in the art will understand that other materials may be employed such as, for example, carbon fiber, PEEK, glass filled epoxy and spring stainless steel.

The first support portion 42 of this embodiment includes fillets 48 on proximal and distal sides thereof to gradually transition from the smaller diameter of the surrounding portions of the distal portion 40 to the increased diameter of the first support portion 42. In this embodiment, the fillets 48 form a portion of a cone having an apex angle of approximately 30° so that the surfaces of the fillets 48 diverge from the cylindrical surface of the increased diameter first support portion 42 by an angle α of approximately 15°. The second support portion 44 also includes a similar fillet 50 on a proximal side thereof which in this embodiment is angled similarly to the fillets 48 so that the surface of the fillet 50 diverges from the cylindrical surface of the increased diameter second support portion 44 by an angle β of approximately 15°. However, those skilled in the art will understand that these angles α and β may be altered as desired without departing from the scope of the embodiments. The second support portion 44 extends to a distal end 52 at which it meets a radially extending abutment surface formed by the increased diameter at the proximal end of a distal tip 32.

The radially extending abutment surface of the distal tip 32 has a diameter greater than a diameter of the distal end of the lumen 24 so that the distal tip 32 cannot be drawn proximally into the lumen 24. The distal tip 32 in this embodiment is rounded so provide an atraumatic distal end to the shaft 10. Those skilled in the art will understand that the flexibility permitted and the support provided to the shaft 10 by the rod 30 will vary based on the difference in the outer diameter of the smaller diameter portions of the distal portion 40 and the inner diameter of the shaft 10 (i.e., the depth of the annular gap between the distal portion 40 and the shaft 10) and the length of the first support portion 42 relative to the length of the flexible portion 16 of the shaft 10. That is, the flexibility and support of the combined shaft 10 and rod 30 will vary depending on the depth and total length of the annular gap between the rod 30 and the inner surface of the flexible portion 16 of the shaft 10.

In use, the shaft 10 is slid distally over the rod 30 until the distal tip 32 is seated at the distal end of the shaft 10. The combined shaft 10/rod 30 is then inserted into the body, through the lumen of an IM nail until the distal coupling 20 at the distal end 22 of the shaft 10 engages a set screw in the IM nail. Those skilled in the art will understand that, while these embodiments are discussed in regard to the engagement of a set screw with the IM nail, the system may be used in a similar manner with any other locking mechanism or other device that needs to be engaged with the IM nail. Torque may then be applied to the proximal 12 of the shaft 10 to rotate the set screw into engagement with, for example, a trochanteric implant to be locked into a desired position within the IM nail. Alternatively, a surgeon may insert the rod 30 into the proximal end of the IM nail and then slide the shaft 10 distally over the rod 30 to guide the shaft 30 into the IM nail.

Figure 7:
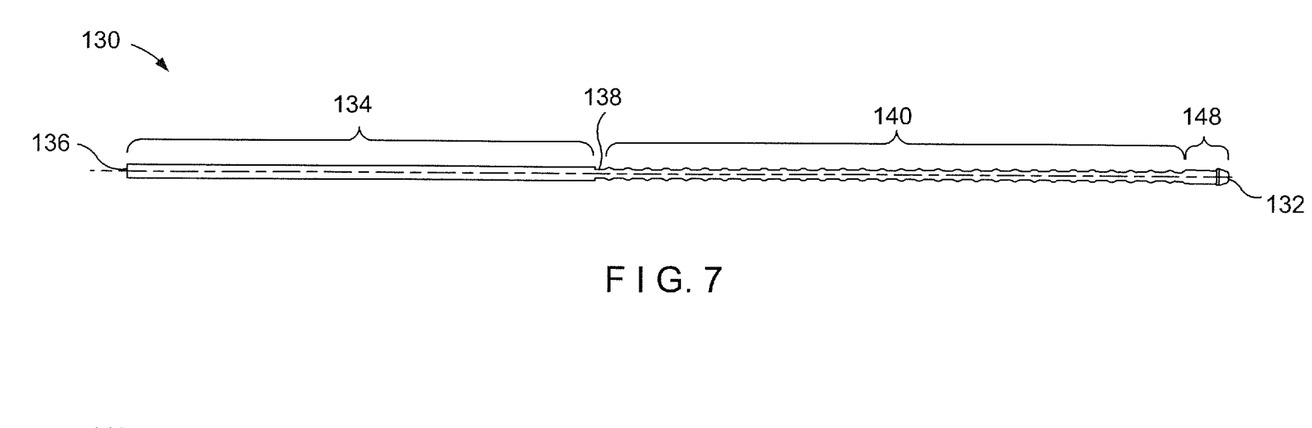
FIG. 7 shows a side view of a support rod according to a second embodiment.
Figure 8:
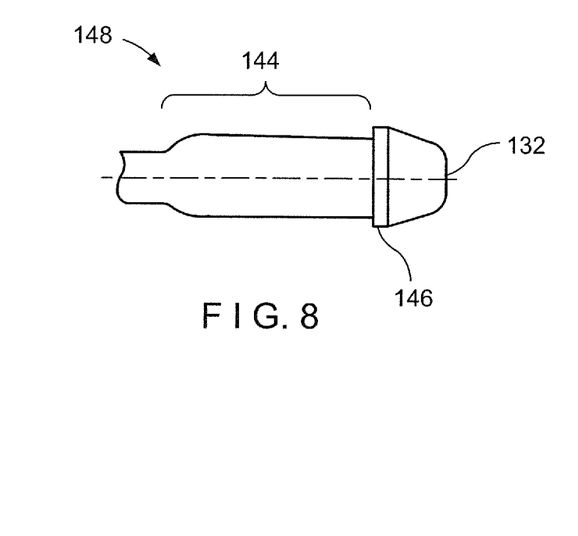
FIG. 8 shows a close up of a distal end of the rod of FIG. 7.
Figure 9:
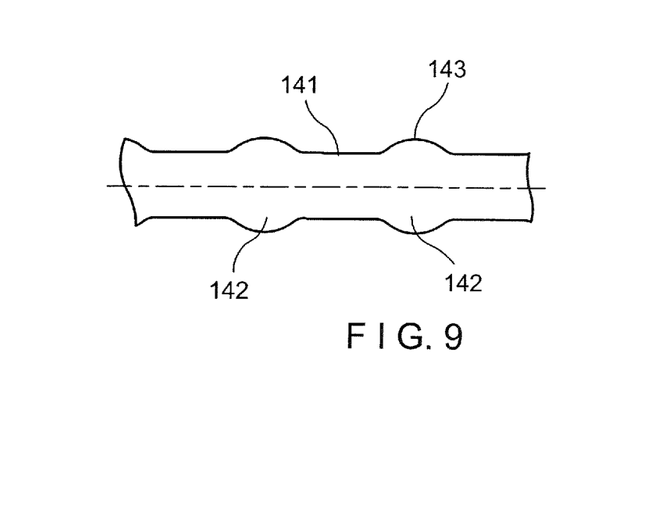
FIG. 9 shows a close up of an increased diameter section of the rod of FIG. 7.

FIGS. 7-9, show a rod 130 according to a second embodiment for use in conjunction with the shaft 10. The rod 130 is substantially similar to the rod 30 except as described below. The rod 130 is also a malleable or low flex strength rod that will support the shaft 10 to prevent coiling/pig-tailing and to ensure the transmission of torque along the length of the shaft 10 while permitting the shaft 10 to bend as necessary to reach desired target areas within the body. The support rod 130 is sized to be inserted within the lumen 24 so that a distal end distal tip 132 of the rod 130 is seated at a distal end of the lumen 24 and projects slightly from the distal end 22 of the shaft 10. As shown in FIG. 7, the rod 130 includes a large diameter portion 134 that extends from a proximal end 136 to a shoulder 138 that necks the outer diameter of the rod 130 down from the increased diameter of the large diameter portion 134 to a reduced, minimum diameter of a distal portion 140. The distal portion 140 of this embodiment has a diameter that varies in an undulating pattern from the minimum diameter at troughs 141 to a maximum diameter at peaks 143.

As seen in FIG. 9, each the trough 141 is themed as a substantially cylindrical reduced diameter portion extending between generally spherical support portions 142 that have a maximum diameter substantially equal to the diameter of the large diameter portion 134. In this embodiment, the diameter of the troughs 141 is approximately 50 to 75% of the diameter of the peaks 143 while the troughs 141 are approximately 1 to 4 times the diameter of the peaks 143 while the support portions 142 are approximately 95% of the inner diameter of the shaft 10. Thus, as the flexible portion 16 of the shaft 10 extends over the distal portion 140 of the rod 130, annular gaps are formed at locations adjacent to the troughs 141 while the shaft 10 is supported by the rod 30 at the peaks 143 in the same manner described above in regard to the rod 30 and the first support portion 42. Although in this embodiment the support portions 142 are distributed substantially evenly along the length of the distal portion 140, those skilled in the art will understand that these support portions 142 may be distributed in any desired pattern and number to obtain the required support while permitting the shaft 10 to bend as required for a particular procedure. As with the rod 30, the support portions 142 of this embodiment have an outer diameter substantially equal to that of the large diameter portion 134 so that, when the rod 130 is seated in the shaft 10 as desired, the large diameter portion 134 fits snugly within the lumen 24 while a gap is formed between those parts of the distal portion 140 overlying the troughs 141 while the support portions 142 fit snugly within the lumen 24.

In addition, the distal portion 140 is positioned along the rod 130 so that, when the rod 130 is positioned within the shaft 10 with the distal tip 132 seated at the distal end of the lumen 24, the distal portion 140 extends within the flexible portion 16 of the shaft 10. The reduced diameter of the troughs 141 of the distal portion 140 form annular gaps between the inner surface of the shaft 10 and the outer surface of the rod 130. These gaps permit the flexible shaft 10 to bend around tight bending radii while the snug fit of the support portions 142 support the shaft 10 preventing the shaft 10 from pig-tailing and facilitating the transfer of torque along the shaft 10. The rod 130 is also preferably malleable or of low flex strength and formed of, for example, nitinol or 304 annealed stainless steel. The rod 130 also includes a short large diameter section 144 extending distally from a distal end of the distal portion 140 to a radially extending abutment surface 146 formed by the increased diameter at the proximal end of a distal portion 148. The radially extending abutment surface 146 of the distal tip distal portion 148 has a diameter greater than a diameter of the distal end of the lumen 24 so that the distal portion 148 can not be drawn proximally into the lumen 24. The distal portion 148 in this embodiment is rounded so provide an atraumatic distal end to the shaft 10.

Figure 10:
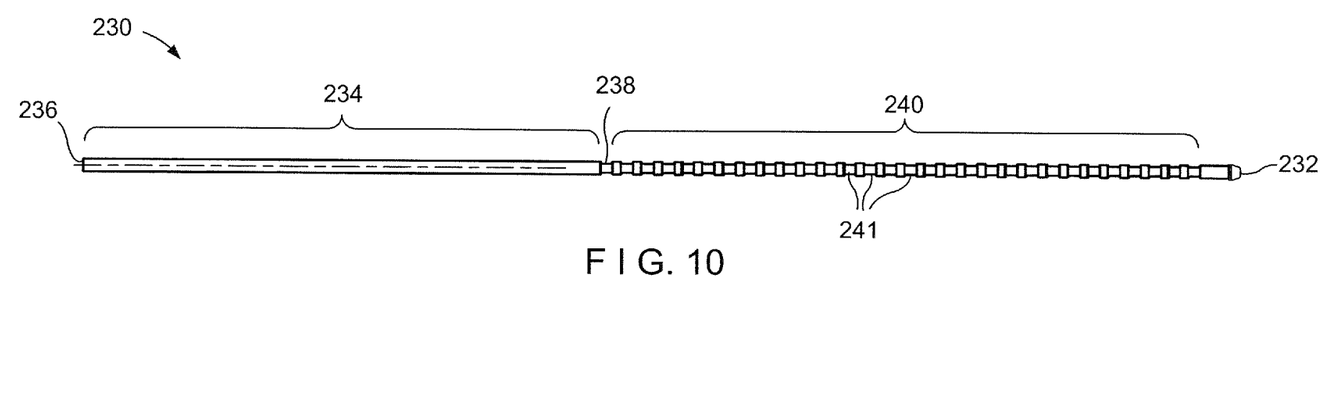
FIG. 10 shows a side view of a flexible rod according to a further embodiment.
Figure 11:
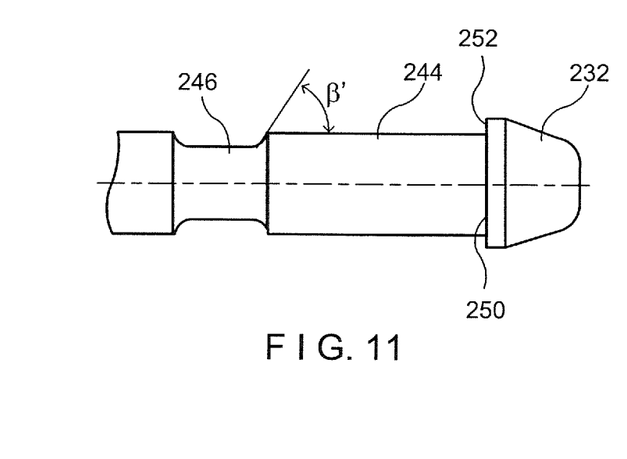
FIG. 11 shows a close up of a distal end of the rod of FIG. 10.
Figure 12:
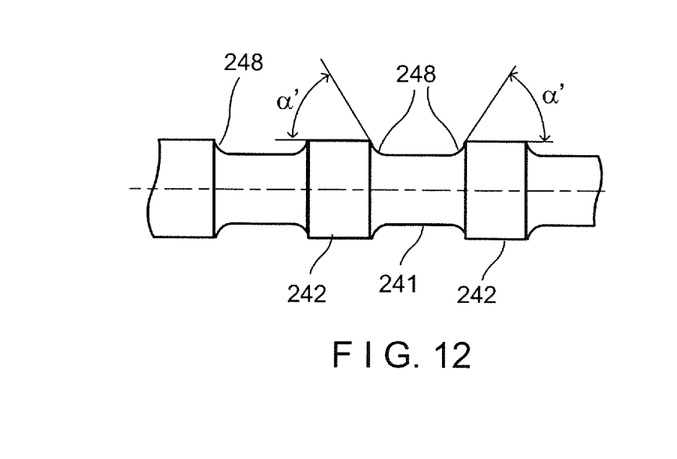
FIG. 12 shows a close up of an increased diameter section of the rod of FIG. 10.

FIGS. 10-12, show a rod 230 according to a third embodiment for use in conjunction with the shaft 10. The rod 230 is substantially similar to the rod 130 except as described below.

The rod 230 is also a malleable or low flex strength rod that will support the shaft 10 to prevent coiling/pig-tailing and to ensure the transmission of torque along the length of the shaft 10 while permitting the shaft 10 to bend as necessary to reach desired target areas within the body. The support rod 230 is sized to be inserted within the lumen 24 so that a distal tip 232 of the rod 230 is seated at a distal end of the lumen 24 and projects slightly from the distal end 22 of the shaft 10. As shown in FIG. 10, the rod 230 includes a large diameter portion 234 that extends from a proximal end 236 to a shoulder 238 that necks the outer diameter of the rod 230 down from the increased diameter of the large diameter portion 234 to a reduced, minimum diameter of the distal portion 240. The distal portion 240 of this embodiment has a diameter that varies in from a minimum diameter at troughs 241 to increased diameter portions 242.

As seen in FIG. 12, each the trough 241 is formed as a substantially cylindrical reduced diameter portion extending between increased diameter, generally cylindrical support portions 242 that have a diameter substantially equal to the diameter of the large diameter portion 234. In this embodiment, the troughs 241 may be dimensioned similarly to the troughs 141 although other dimensions may be employed without departing from the teachings of this disclosure. The increased diameter portions 242 of this embodiment include fillets 248 on proximal and distal sides thereof to gradually transition from the smaller diameter of the troughs 241 to the increased diameter of the increased diameter portions 242. In this embodiment, the fillets 248 form a portion of a cone having an apex angle of approximately 120° so that the surfaces of the fillets 248 diverge from the cylindrical surface of the increased diameter portions 242 by an angle α' of approximately 60°. The distal tip 232 of the rod 230 includes a support portion 244 that also includes a fillet 246 on a proximal side thereof which in this embodiment is angled similarly to the fillets 248 so that the surface of the fillet 246 diverges from the cylindrical surface of the support portion 244 by an angle β' of approximately 60°.

However, those skilled in the art will understand that these angles α' and β' may be altered as desired without departing from the scope of the embodiments. The support portion 244 extends to a distal end 250 at which it meets a radially extending abutment surface 252 formed by the increased diameter at the proximal end of a distal tip 232. The radially extending abutment surface of the distal tip 252 has a diameter greater than a diameter of the distal end of the lumen 24 so that the distal tip 252 cannot be drawn proximally into the lumen 24. The distal tip 252 in this embodiment is rounded so provide an atraumatic distal end to the shaft 10. Those skilled in the art will understand that the length of and spacing between the increased diameter portions 242 may be varied as desired to achieve a desired balance of support for the shaft 10 and flexibility for the combination of the shaft 10 and the rod 230. In addition, the increased diameter portions may vary in length and spacing over the length of the distal portion 240 in any desired pattern to achieve the desired response of the combination of the rod 230 and the shaft 10.

Thus, as the flexible portion 16 of the shaft 10 extends over the distal portion 240 of the rod 230, annular gaps are formed at locations adjacent to the troughs 241 while the shaft 10 is supported by the rod 230 by the support portions 242 in the same manner described above in regard to the rod 130 and the first support portion 142. Although in this embodiment the support portions 142 are distributed substantially evenly along the length of the distal portion 240, those skilled in the art will understand that these support portions 242 may be distributed in any desired pattern and number to obtain the required support while permitting the shaft 10 to bend as required for a particular procedure.

As with the rod 130, the support portions 242 of this embodiment have an outer diameter substantially equal to that of the large diameter portion 234 so that, when the rod 230 is seated in the shaft 10 as desired, the large diameter portion 234 fits snugly within the lumen 24 while a gap is formed between those parts of the distal portion 240 overlying the troughs 241 while the support portions 242 fit snugly within the lumen 24. In addition, the distal portion 240 is positioned along the rod 230 so that, when the rod 230 is positioned within the shaft 10 with the distal tip 232 seated at the distal end of the lumen 24, the distal portion 240 extends within the flexible portion 16 of the shaft 10. The reduced diameter of the troughs 241 of the distal portion 240 form annular gaps between the inner surface of the shaft 10 and the outer surface of the rod 230. These gaps permit the flexible shaft 10 to bend around tight bending radii while the snug fit of the support portions 242 support the shaft 10 preventing the shaft 10 from pig-tailing and facilitating the transfer of torque along the shaft 10. The rod 230 is also preferably malleable or of low flex strength and formed of, for example, nitinol or 304 annealed stainless steel.

The rod 230 also includes a short large diameter section 244 extending distally from a distal end of the distal portion 240 to a radially extending abutment surface 246 formed by the increased diameter at the proximal end of a distal portion 248. The radially extending abutment surface 246 of the distal portion 248 has a diameter greater than a diameter of the distal end of the lumen 24 so that the distal portion 248 cannot be drawn proximally into the lumen 24. The distal portion 248 in this embodiment is rounded so provide an atraumatic distal end to the shaft 10. In addition, those skilled in the art will understand that the angles of the fillets in the various embodiments may be selected to enhance the cleanability of the item (for re-use), ease of manufacture.

Figure 13:
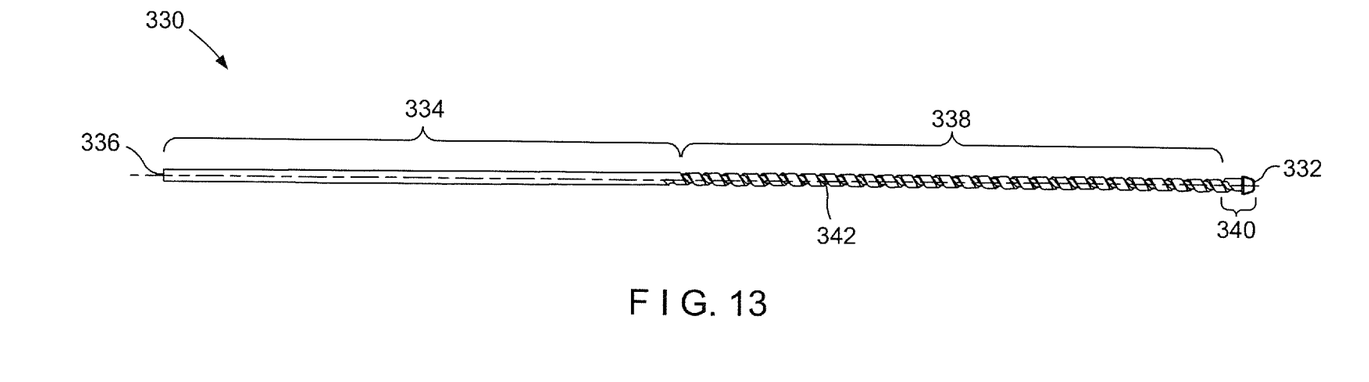
FIG. 13 shows a side view of a support rod according to a still further embodiment.
Figure 14:
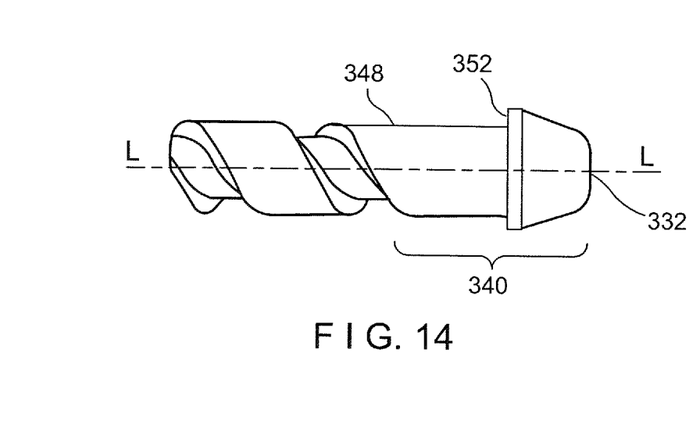
FIG. 14 shows a close up of a distal end of the rod of FIG. 13.
Figure 15:
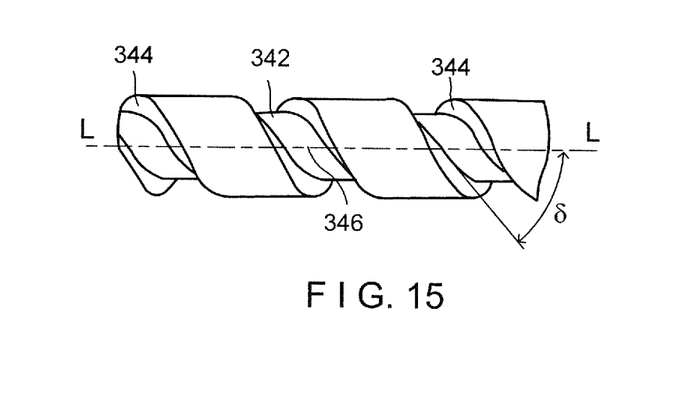
FIG. 15 shows a close up of an increased diameter section of the rod of FIG. 13.

FIGS. 13-15 show a rod 330 according to a fourth embodiment for use in conjunction with the shaft 10. The rod 330 is substantially similar to the rod 130 except as described below.

The rod 330 is also a malleable or low flex strength rod that will support the shaft 10 to prevent coiling/pig-tailing and to ensure the transmission of torque along the length of the shaft 10 while permitting the shaft 10 to bend as necessary to reach desired target areas within the body. The support rod 330 is sized to be inserted within the lumen 24 so that a distal tip 332 of the rod 330 is seated at a distal end of the lumen 24 and projects slightly from the distal end 22 of the shaft 10. As shown in FIG. 13, the rod 330 includes a support portion 334 that extends from a proximal end 336 to a flex portion 338 extending from the distal end of the support portion 334 of the rod 330 to a distal portion 340 of the rod 330. The flex portion 338 of this embodiment includes a helical groove 342 running along its length so that a diameter of the rod 330 in the flex portion 338 varies between a first diameter substantially equal to the diameter of the support portion 334 and a second diameter less than the first diameter within the groove 342.

As seen in FIG. 15, the groove 342 of this embodiment is with walls 344 that extend substantially perpendicularly away from the radially inner-most surface 346 of the groove 342. Thus, the length of the groove 342 forms a helical gap between the rod 330 and the inner surface of the shaft 10 that is substantially equal in depth to a depth of the groove 342. In this embodiment, the groove 342 is approximately 1 to 4 times the diameter of the support portions 348 and a helix angle δ of this groove 342 relative to a longitudinal axis L of the rod 330. Those skilled in the art will recognize, however, that the width and angle δ of the groove 342 may be varied to achieve the desired balance between support provided to and flexibility permitted to the shaft 10. The distal portion 340 of the rod 330 includes a support portion 348 extending to a distal tip 350 which forms a radially extending abutment surface 352 formed by the increased diameter at the proximal end of the distal tip 350. The radially extending abutment surface 352 of the distal tip 350 has a diameter greater than a diameter of the distal end of the lumen 24 so that the distal tip 350 cannot be drawn proximally into the lumen 24. The distal tip 332 in this embodiment is rounded so provide an atraumatic distal end to the shaft 10. Although in this embodiment the groove 342 extends along the distal portion 340 at a constant helix angle δ, those skilled in the art will understand that this angle may be varied in any manner to achieve the desired balance of flexibility and support along the flexible portion 16 of the shaft. enhance the cleanability of the item (for re-use), ease of manufacture.

Although these embodiments have been described in connection with the application of this support rod in a flexible shaft serving as a flexible screw driver to drive a set screw in an IM nail, those skilled in the art will understand that this structure may be used in conjunction with a hollow shaft that is required to transmit torque over a non-straight path (e.g., which requires axial flexibility) while supporting the shaft against coiling/pig-tailing. For example, a support rod according to any of the embodiments may be used in conjunction with a flexible drill or reamer for, example, drilling out or reaming small bones such as the clavicle, ulna, humerus, etc.

In addition, although specific embodiments and methods have been described, it will be appreciated that various modifications other than those discussed above may be resorted to without departing from the spirit or scope of the invention as defined in the appended claims. For example, equivalent elements may be substituted for those specifically shown and described, certain features may be used independently of other features, and in certain cases, particular applications of elements may be reversed or interposed, all without departing from the spirit or scope of the invention.

What is claimed is:

1. A support rod configured for use with a hollow, flexible torque transmitting shaft for treating a bone, comprising:
    a proximal portion configured so that, when the support rod is received at a desired position within the shaft, the proximal portion of the support rod extends through a proximal portion of a length of the shaft that is not configured to bend in use, an outer diameter of the proximal portion substantially corresponding to an inner diameter of a proximal portion of a lumen of the shaft to support the proximal portion of the shaft; and a distal portion configured so that, when the support rod is received at the desired position within the shaft, the distal portion of the support rod extends through a second distal portion of a length of the shaft that is configured to bend in use, the distal portion of the support rod including a holding portion having an outer diameter substantially corresponding to an inner diameter of a distal portion of the second portion lumen of the shaft and a gap portion having an outer diameter reduced relative to the outer diameter of the holding portion to form an annular gap between the gap portion and an inner surface of the holding portion the distal portion of the lumen of the shaft.

2. The rod of claim 1, further comprising:
a distal end extending distally from the distal portion of the support rod and including a distal tip having an outer diameter greater than a diameter of a distal opening of the shaft.

3. The rod of claim 2, wherein the proximal portion of the shaft is relatively rigid and the distal portion of the shaft is flexible, the proximal portion of the support rod is configured so that, when the support rod is inserted into the shaft, the distal tip is seated against a distal end of the shaft, the proximal portion of the support rod resides within the proximal portion of the lumen of the shaft and the distal portion of the support rod resides within the distal portion of the lumen of the shaft.

4. The rod of claim 2, wherein the holding portion includes a plurality of supports separated from one another and the gap portion includes a plurality of reduced diameter sections separating the supports from one another along a length of the distal portion of the support rod.

5. The rod of claim 4, wherein a first one of the supports is substantially cylindrical and is coupled to adjacent ones of the reduced diameter sections via proximal and distal fillets.

6. The rod of claim 5, wherein the distal end of the support rod includes a substantially cylindrical distal end support coupled to a distal-most one of the reduced diameter sections via a fillet, an outer diameter of the distal end support being substantially equal to the outer diameters of the supports of the holding portion.

7. The rod of claim 6, wherein the distal end support extends distally from a proximal end to a distal end abutting a proximal end of the distal tip, the proximal end of the distal tip forming a radially protruding abutment having a diameter greater than a diameter of the distal opening of the shaft.

8. The rod of claim 1, wherein the support rod is foiined of one of nitinol and malleable stainless steel.

9. The rod of claim 8, wherein the malleable stainless steel is 304 annealed stainless steel.

10. A system for treating a bone, comprising:
a hollow, flexible torque ransmitting shaft; and
a support rod sized and shaped to be received within the shaft, the support rod including a proximal portion configured so that, when the support rod is received at a desired position within the shaft, the proximal portion of the support rod extends through a proximal portion of a length of the shaft that is not configured to bend in use, an outer diameter of the proximal portion of the support rod substantially corresponding to an inner diameter of a proximal portion of a lumen of the shaft to support the proximal portion of the shaft and a distal portion configured so that, when the support rod is received at the desired position within the shaft, the distal portion of the support rod extends through a distal portion of a length of the shaft that is configured to bend in use, the distal portion of the support rod including a holding portion having an outer diameter substantially corresponding to an inner diameter of a distal portion of the lumen of the shaft and a gap portion having an outer diameter reduced relative to the outer diameter of the holding portion to form an annular gap between the gap portion and an inner surface of the distal portion of the lumen of the shaft.

11. The system of claim 10, wherein the support rod comprises a distal end extending distally from the distal portion of the support rod and including a distal tip having an outer diameter greater than a diameter of a distal opening of the shaft, the distal end of the support rod being configured to seat against a distal end of the shaft when the support rod is in the desired position.

12. The system of claim 11, wherein the proximal portion of the shaft is relatively rigid and the distal portion of the shaft is flexible, the proximal portion of the support rod is configured so that, when the support rod is inserted into the shaft, the distal tip is seated against the distal end of the shaft, the proximal portion of the support rod resides within the proximal portion of the lumen of the shaft and the distal portion of the support rod resides within the distal portion of the lumen of the shaft.

13. The system of claim 11, wherein the holding portion includes a plurality of supports separated from one another and the gap portion includes a plurality of reduced diameter sections separating the supports from one another along a length of the distal portion of the support rod.

14. The system of claim 13, wherein a first one of the supports is substantially cylindrical and is coupled to adjacent ones of the reduced diameter sections via proximal and distal fillets.

15. The system of claim 14, wherein the distal end of the support rod includes a substantially cylindrical distal end support coupled to a distal-most one of the reduced diameter sections via a fillet, an outer diameter of the distal end support being substantially equal to the outer diameters of the supports of the holding portion.

16. The system of claim 15, wherein the distal end support extends distally from a proximal end to a distal end abutting a proximal end of the distal tip, the proximal end of the distal tip forming a radially protruding abutment having a diameter greater than a diameter of the distal opening of the shaft.

17. The system of claim 10, wherein the support rod is folioed of one of nitinol and malleable stainless steel.

18. The system of claim 17, wherein the malleable stainless steel is 304 annealed stainless steel.

* * * * *

UNITED STATES PATENT AND TRADEMARK OFFICE
CERTIFICATE OF CORRECTION

| | |
|---|---|
| PATENT NO. | : 11,446,073 B2 |
| APPLICATION NO. | : 16/551154 |
| DATED | : September 20, 2022 |
| INVENTOR(S) | : Kmiec, Jr. et al. |

It is certified that error appears in the above-identified patent and that said Letters Patent is hereby corrected as shown below:

In the Claims

Claim 8, Column 9, Line 47:
"8. The rod of claim 1, wherein the support rod is foiined" should read "8. The rod of claim 1, wherein the support rod is formed".

Claim 10, Column 9, Line 52:
"a hollow, flexible torque ransmitting shaft; and" should read "a hollow, flexible torque transmitting shaft; and".

Claim 17, Column 10, Line 54:
"folioed of one of nitinol and malleable stainless steel." should read "formed of one of nitinol and malleable stainless steel.".

Signed and Sealed this
First Day of November, 2022

*Katherine Kelly Vidal*

Katherine Kelly Vidal
*Director of the United States Patent and Trademark Office*